US006322772B1

(12) United States Patent
Wehrli

(10) Patent No.: US 6,322,772 B1
(45) Date of Patent: Nov. 27, 2001

(54) METHODOLOGY FOR TREATMENT OF THE DENTAL ARCHES AND PERIODONTAL TISSUE

(76) Inventor: Janet Margaret Wehrli, 6737 S. 153 Cir., Omaha, NE (US) 68137

( * ) Notice: Subject to any disclaimer, the term of this patent is extended or adjusted under 35 U.S.C. 154(b) by 0 days.

(21) Appl. No.: 09/549,301

(22) Filed: Apr. 13, 2000

Related U.S. Application Data

(60) Provisional application No. 60/145,028, filed on Jul. 22, 1999.

(51) Int. Cl.$^7$ .............................. A61K 7/16; A61K 5/00; A61K 5/14
(52) U.S. Cl. ............................. 424/49; 433/80; 433/215; 433/216; 128/848; 128/859; 128/861; 128/862
(58) Field of Search ........................... 424/49–88, 802.16, 424/215

(56) References Cited

U.S. PATENT DOCUMENTS

| | | | |
|---|---|---|---|
| 3,339,547 | * 9/1967 | Drabkowski | 128/260 |
| 3,527,219 | * 9/1970 | Greenborg | 128/260 |
| 3,844,286 | * 10/1974 | Cowen | 128/260 |
| 4,344,931 | * 8/1982 | Aguilar | 424/49 |
| 4,812,308 | * 3/1989 | Winston et al. | 424/49 |
| 4,813,613 | * 3/1989 | Sauete | 241/7 |
| 4,981,698 | * 1/1991 | Cherukuri et al. | 426/5 |
| 5,004,595 | * 4/1991 | Cherukuri et al. | 424/49 |
| 5,038,396 | * 8/1991 | Gjerlov | 424/737 |
| 5,143,728 | * 9/1992 | Cappel et al. | 424/195.1 |
| 5,294,432 | * 3/1994 | Winston et al. | 424/49 |
| 5,323,787 | * 6/1994 | Pratt | 128/862 |
| 5,445,826 | * 8/1995 | Kuhrtz | 424/451 |
| 5,466,469 | * 11/1995 | Kuhrtz | 424/451 |
| 5,575,654 | * 11/1996 | Fontenot | 433/215 |
| 5,863,202 | * 1/1999 | Fontenot | 433/215 |
| 5,869,029 | * 2/1999 | Grarf-Andersen et al. | 424/52 |
| 5,948,439 | * 9/1999 | Forman et al. | 424/466 |
| 6,086,856 | * 7/2000 | Saferstein et al. | 424/49 |
| 6,258,342 | * 7/2001 | Harcum et al. | 424/49 |

FOREIGN PATENT DOCUMENTS

2000044446 * 2/2000 (JP).

* cited by examiner

*Primary Examiner*—Shep K. Rose

(57) ABSTRACT

A dentifrice form consisting of a dry compound of sodium bicarbonate as an oral bactricidal agent and oral antacid, psyllium husk fiber as a delivery system being an absorbent expansive binder and a flavoring agent. The dentifrice form is then placed in a porous dental mouth tray which is lined with a permeable matrix moistened with potable water. The dentifrice form in the tray is then moistened with potable water and the tray with the moistened dentifrice form is inserted into the oral cavity and placed against the upper or lower dental arch so as to cause the dentifrice form to be in contact with the teeth and gums of the respective arch for a period of seven minutes. The process is then repeated for the remaining dental arch.

1 Claim, No Drawings

METHODOLOGY FOR TREATMENT OF THE DENTAL ARCHES AND PERIODONTAL TISSUE

This application claims benefit of Provisional Application No. 60/145,028, filed Jul. 22, 1999.

BACKGROUND OF THE INVENTION

The present invention is directed generally to a dentifrice form, methodology of application, delivery system, and action for cleaning the oral cavity and the intraoral structures and more particularly to the use of a tray in which the dentifrice form is placed in one or more layers and which is then placed in contact with the teeth, gums and intraoral structures of the oral cavity for a specific time period.

Dentifrice 'form' is generally accepted to mean liquids, powders, gels, or pastes used to clean the teeth, gums and other structures within the oral cavity.

Dentifrice 'application' is generally accepted to mean methods used to apply dentifrice forms to the structures within the oral cavity. Common methods include the use of a toothbrush, dental floss, rinsing with liquids and high pressure sprays. Less common methods include impregnated self sticking strips and dentifrice form impregnated finger cots.

Dentifrice "delivery system" in the present instance means the technology or device by which the ingredients of the dentifrice form are physically delivered or transferred so as to act in the desired manner upon the teeth, gums and structures within the oral cavity.

Dentifrice 'action' is generally accepted to mean the amount of cleansing accomplished by a dentifrice form and its methodology of application to the structures within the oral cavity.

A problem with conventional dentifrice forms, their application, delivery system, and action is that it is difficult to reach all areas of the teeth, gums and surrounding structures of the oral cavity due to the nature and structure of the oral cavity and the dental arch.

Another problem with conventional dentifrice forms, their application, delivery system, and action is that the flow of crevicular fluid in the oral cavity tends to dilute and diminish the dentifrice form, thereby diminishing the dentifrice forms action.

Another problem with conventional dentifrice forms, their application, delivery system, and action is the difficulty of applying the dentifrice form for those who are unable to use common methods of dentifrice form application.

Another problem is ensuring the safety of the user if the dentifrice form is inadvertently ingested by the user.

Another problem is to ensure compatibility of the dentifrice form, delivery system, and action with fluoride.

Another problem is to ensure that the dentifrice form, delivery system, and action minimizes acidic action in the oral cavity.

Whereas Sodium Bicarbonate ($NaHCO_3$) is a substance that occurs naturally and that has long been used to clean teeth and is recognized in sustained high concentrations to be a specific time-sensitive bactericidal agent effective against most periodontal pathogens and whereas Psyllium Husk fiber is a natural fiber with the property of being highly hygroscopic and is currently used internally by human beings to lower cholesterol and as a bulk forming laxative. The use of sodium bicarbonate in combination with Psyllium Husk fiber has not previously been used in a dentifrice form and/or delivery system.

Accordingly the primary object of the present improved dentifrice form, method of application, and delivery system is to provide a utility wherein the dentifrice form and action are minimally degraded by the oral environment and are thus able to sustain a high concentration of the dentifrice form within the oral cavity for a measured period of time to effect elimination and destruction of periodontal pathogens to a degree heretofore achieved only through professional dental services.

Another object is to provide an improved dentifrice form, method of application, delivery system, and action to aid individuals unable to utilize a toothbrush, dental floss or other traditional means of cleaning the oral cavity and the structures therein.

Another object is to provide an improved dentifrice form, method of application, and delivery system, to deliver a high concentration of sodium bicarbonate to the oral cavity and the structures therein to reduce periodontal pathogens.

Another object is to provide an improved dentifrice form, method of application, delivery system and action that will minimize mechanical damage and irritation to the tissue and structures of the oral cavity.

Another object is to provide an improved dentifrice form, method of application, delivery system and action, which will be minimally abrasive to the dentin and enamel of the teeth.

Another object is to provide an improved dentifrice form, method of application, delivery system and action that will minimize the need for antibiotics and their possible side effects in the treatment of periodontal disease.

Another object is to provide an improved dentifrice form which is economical to manufacture and efficient in operation.

Finally, another object is to provide a delivery system wherein sodium bicarbonate or other medically beneficial substances can be delivered orally to patients without being substantially diluted or diminished by the flow of oral fluids in the oral cavity.

SUMMARY OF THE INVENTION

The dentifrice form of the present invention consists of a compound of sodium bicarbonate, powdered psyllium husk fiber and a flavoring agent.

The dentifrice form is utilized as follows:

1. A porous dental mouth tray commonly utilized for dental impressions is covered with a permeable matrix.
2. A sufficient amount of potable water is then utilized to dampen the permeable matrix which is then fitted to the dental mouth tray.
3. The dentifrice form is then placed into the dental mouth tray on top of the moist permeable matrix and is then dampened with potable water.

The mouth tray is then inserted into the oral cavity and placed on either the upper or lower dental arch and fitted to the teeth and gums by the user so as to cause the dentifrice form to be in contact with the teeth and gums. The tray and its contents is then held in position for a period of not less than seven minutes. The upper and lower dental arch are done in the same manner for the same period of time.

DETAILED DESCRIPTION OF THE INVENTION

The improved dentifrice form consists of a compound of sodium bicarbonate, powdered psyllium husk fiber, and flavoring agent which is placed so as to fill in a porous dental mouth tray lined with a moist permeable matrix. When that is done, the tray with the improved dentifrice form is inserted in the oral cavity and placed on either the upper or lower dental arch and fitted to the teeth and gums so that full contact is made with the teeth and gums. The tray is then held in position for not less than seven minutes and removed from the oral cavity. The tray and remaining contents are then discarded or the tray is washed for future use. The process is repeated again so that the remaining dental arch is treated in the same manner for not less than seven minutes. The tray is then removed from the oral cavity and the tray and its remaining contents are discarded, or the dentifrice and permeable matrix are discarded, and the tray is washed for future use. The mouth is then rinsed with potable water to remove any dentifrice form residue.

Whereas the invention is shown and described in connection with the preferred method of utilization, it is understood that many modifications, substitutions and additions may be made which are within the intended broad scope of the appended claims.

Thus there has been shown and described an improved dentifrice form and method of application and delivery system which accomplishes at least all of the stated objects.

I claim:

1. In the method of contacting periodontal pathogens with sodium bicarbonate, the improvement comprising the following steps:
   (1) moisten with water a porous dental tray lined with a permeable matrix, to dampen the permeable matrix;
   (2) dry admix (A) dry sodium bicarbonate, a bactericidal agent effective against periodontal pathogens, with (b) dry psyllium husk fiber, imparting moisture absorbing, expanding and mucilaginous properties, and (c) flavoring agent,
   (3) insert the filled dental tray into the oral cavity;
   (4) place it on either the upper or lower dental arch;
   (5) fit it to contact the teeth and gums for not less than seven minutes,
   (6) remove the tray and its remaining contents;
   (7) repeat the procedure for the remaining dental arch
   (8) rinse the mouth with potable water to remove any residue;
   (9) discard the dental tray, or
   (10) wash the tray for future use.

* * * * *